United States Patent
Mitra et al.

(10) Patent No.: US 7,345,280 B2
(45) Date of Patent: Mar. 18, 2008

(54) MEASUREMENT OF STEAM QUALITY USING MULTIPLE BROADBAND LASERS

(75) Inventors: Chayan Mitra, Bangalore (IN); Mark A Woodmansee, Minden, NV (US); Ayan Banerjee, Bangalore (IN)

(73) Assignee: General Electric Company, Schenectady, NY (US)

( * ) Notice: Subject to any disclaimer, the term of this patent is extended or adjusted under 35 U.S.C. 154(b) by 188 days.

(21) Appl. No.: 11/162,969

(22) Filed: Sep. 29, 2005

(65) Prior Publication Data

US 2007/0069132 A1    Mar. 29, 2007

(51) Int. Cl.
    *G01J 5/02*    (2006.01)
(52) U.S. Cl. ...................................... 250/345
(58) Field of Classification Search ................. 250/345
    See application file for complete search history.

(56) References Cited

U.S. PATENT DOCUMENTS

| | | | |
|---|---|---|---|
| 4,137,462 A | 1/1979 | Wyler | |
| 4,497,577 A | 2/1985 | Sato et al. | |
| 4,574,626 A | 3/1986 | Kaya et al. | |
| 4,712,006 A | 12/1987 | Zemel et al. | |
| 4,832,503 A | 5/1989 | Dowling et al. | |
| 4,862,001 A | 8/1989 | Dowling et al. | |
| 4,969,084 A | 11/1990 | Smith | |
| 5,220,168 A | 6/1993 | Adamski et al. | |
| 5,327,772 A | 7/1994 | Fredricks | |
| 5,509,478 A | 4/1996 | Stoy | |
| 5,825,478 A | 10/1998 | Wilcox et al. | |
| 5,870,926 A | 2/1999 | Saito et al. | |
| 6,128,079 A | 10/2000 | McCloskey et al. | |
| 6,188,705 B1 * | 2/2001 | Krainak et al. | ................ 372/32 |
| 6,250,131 B1 | 6/2001 | Pauley et al. | |
| 6,445,565 B1 | 9/2002 | Toyoda et al. | |
| 6,502,456 B1 | 1/2003 | Chen | |
| 6,885,453 B2 * | 4/2005 | Kaufmann | ................... 356/439 |
| 7,034,302 B2 * | 4/2006 | Davidson et al. | ......... 250/339.1 |
| 2002/0108431 A1 | 8/2002 | Hoffman | |
| 2003/0015024 A1 | 1/2003 | Campbell et al. | |
| 2003/0069674 A1 | 4/2003 | Stam et al. | |
| 2003/0139687 A1 | 7/2003 | Abreu | |

(Continued)

FOREIGN PATENT DOCUMENTS

CN        1263263 A        8/2000

(Continued)

*Primary Examiner*—David Porta
*Assistant Examiner*—Jessica L Eley
(74) *Attorney, Agent, or Firm*—Sutherland Asbill & Brennan LLP

(57) ABSTRACT

Determination of steam quality by passing one or more laser beams through steam in a steam chamber and directly determining a total number of vapor molecules and a total number of water molecules based on absorption of radiation in the one or more laser beams by the water vapor phase and the liquid water phase in the steam. Specific volumes of water vapor phase and liquid water phase in the steam using the total numbers of water vapor and liquid water molecules are determined and the quality of the steam is calculated based on the specific volumes of the water vapor phase and the liquid water phase in steam. One embodiment comprises a narrow linewidth laser for measuring steam quality and another embodiment comprises multiple broadband lasers for measuring steam quality.

24 Claims, 3 Drawing Sheets

| U.S. PATENT DOCUMENTS | | |
|---|---|---|
| 2003/0151738 A1 | 8/2003 | Chen |
| 2004/0056197 A1 | 3/2004 | Davidson et al. |

FOREIGN PATENT DOCUMENTS

| CN | 1318749 A | 10/2001 |
|---|---|---|
| CN | 1388370 A | 1/2003 |
| GB | 2 281 967 A | 3/1995 |
| WO | WO 01/36951 A2 | 5/2001 |
| WO | WO 01/36951 A3 | 5/2001 |

* cited by examiner

US 7,345,280 B2

MEASUREMENT OF STEAM QUALITY USING MULTIPLE BROADBAND LASERS

TECHNICAL FIELD

This invention relates to production of steam, and more particularly, relates to measuring steam quality.

BACKGROUND OF THE INVENTION

Steam is used in many industrial applications such as heating and power conversion. Under some circumstances, steam includes a water vapor phase, which is gaseous water, and a liquid water phase, which is small droplets of water suspended in the water vapor phase. The amount of liquid water phase relative to the water vapor phase is also called the "wetness factor" or "steam quality" and affects performance of steam in some applications.

For example, steam quality affects performance of steam turbine generators. Specifically, turbine blade performance affects steam turbine generator performance. The thermodynamic and aerodynamic performance of turbine blades are determined in part by the surface finish and shape of the blades which can be affected by steam quality. A steam turbine operating in wet steam conditions has lower thermodynamic efficiency then when operating in dry steam. According to "Baumann's Rule," an increase in steam wetness decreases turbine efficiency. Water droplets from the liquid water phase of steam impact the surface of turbine blades at a high velocity and corrode the blades. Corrosion of turbine blades result in thermodynamic and aerodynamic losses in turbine operation and reduces power output of the steam turbine generator.

Accordingly, it is desirable to be able to measure the quality of steam being used to drive a steam turbine generator as the steam turbine generator is operating. Methods for measuring steam quality exist. One method includes measuring the temperature of wet steam with calorimeters and measuring pressure of the wet steam with pressure gauges. Specific volumes of liquid water and water vapor are determined from steam tables and the steam quality is calculated from those specific volumes.

Therefore, there is a need for an effective and economical apparatus and method for directly measuring steam quality while steam is being used in applications such as in a steam turbine generator.

SUMMARY OF THE INVENTION

This invention addresses the above described need by providing a method and apparatus for directly measuring a total number of steam molecules and a total number of water molecules in steam using one or more laser beams passing through the steam, determining specific volumes of water vapor phase and liquid water phase in the steam using the total numbers of water vapor and liquid water molecules, and calculating the quality of the steam based on the specific volumes of the water vapor phase and liquid water phase in the steam. Such a direct measurement of steam quality is quick, economical, and non-invasive.

According to one embodiment of this invention, a method for determining steam quality is provided comprising the steps of frequency-scanning a laser beam emitted from a narrow linewidth laser along a path through steam in a steam chamber to excite a molecular transition in the steam which has a water vapor phase and a liquid water phase, determining a total number of water vapor molecules in the path of the laser beam based on a normalized peak absorption amplitude of the water vapor phase as the laser beam passes through the steam, determining a total number of liquid water molecules in the laser beam path based on a shift on a dc level of a peak absorption amplitude of the water vapor phase from a dc level of a reference peak absorption amplitude, determining specific volumes of the water vapor phase and the liquid water phase in the steam using the total numbers of water vapor and liquid water molecules, and calculating the quality of the steam based on the specific volumes of water vapor phase and liquid water phase in the steam. This embodiment is capable of directly measuring the steam quality with only a single narrow linewidth laser.

Accordingly to another embodiment of this invention, a system for determining steam quality is provided comprising a chamber for containing steam having a water vapor phase and a liquid water phase, a narrow linewidth laser operatively associated with the chamber for frequency-scanning a laser beam along a path through the steam to excite a molecular transition in the steam, and a device for measuring peak absorption amplitude of the water vapor phase as the laser beam passes through the steam and a shift in dc level of peak absorption amplitude of the water vapor phase from a dc level of a reference peak absorption amplitude. This embodiment is capable of directly measuring steam quality with a single narrow linewidth laser.

According to still another embodiment of this invention, a method for determining steam quality is provided comprising passing a first laser beam at a first wave length emitted from a first broadband laser along a path through steam in a steam chamber, the steam having a water vapor phase and a liquid water phase, and passing a first laser beam at a second wave length emitted from a second broadband laser along a path through the steam in the steam chamber. The first wavelength of the first laser beam is such that the water vapor phase absorbs radiation in the first laser beam at a high level and the liquid water phase absorbs radiation in the first laser beam at a level substantially lower than the high level of absorption of absorption by the water vapor phase. The second wavelength of the second laser beam is different from the first length and is such that the liquid water phase absorbs radiation in the second laser beam at a high level and the water vapor phase absorbs radiation in the second laser beam at a level substantially lower than the high level of absorption by the liquid water phase. The method of this embodiment further comprises measuring the transmitted intensity of the first laser beam through the steam, measuring the transmitted intensity of the second laser beam through the steam, and normalizing the transmitted intensities of the first and second laser beams through the steam. Furthermore, the method of this embodiment comprises using Beer Lambert's law to determine the total number of water vapor molecules in the path of the first laser beam based on the normalized transmitted intensity of the first laser beam through the steam and determining a total number of liquid water molecules in the path of the second laser beam based on the normalized transmitted intensity of the second laser beam through the steam. In addition, the method of this embodiment comprises determining specific volumes of the water vapor phase and the liquid water phase in the steam using the total numbers of water vapor and liquid water molecules and calculating quality of the steam based on the specific volumes of water vapor phase and liquid water phase in the steam.

According to yet another embodiment of this invention, a system for determining steam quality is provided comprising a chamber for containing steam having a water vapor phase and a liquid water phase, a first broadband laser operatively associated with the chamber for passing a first laser beam at a first wavelength along a path through steam in the steam chamber, a second broadband laser operatively associated with the chamber for passing a second laser beam at a second wavelength along a path through steam in the steam chamber, a first photodetector for measuring the transmitted intensity of the first laser beam through the steam, and second photodetector for measuring the transmitted power of the second laser beam through the steam. The first wavelength of the first broadband laser is such that the water vapor phase absorbs radiation in the first laser beam at a high level and the liquid water phase absorbs radiation in the first laser beam at a level substantially lower than the high level of absorption by the water vapor phase, and the second wavelength of the second broadband laser is different from the first wavelength and is such that the liquid water phase absorbs radiation in the second laser beam at a high level and the water vapor phase absorbs radiation in the second laser beam at a level substantially lower than the high level of absorption of the liquid water phase.

Other features of embodiments of this invention will be appreciated from the following detail description of embodiments, drawings, and claims.

DETAILED DESCRIPTION OF EMBODIMENTS

Figure 1:
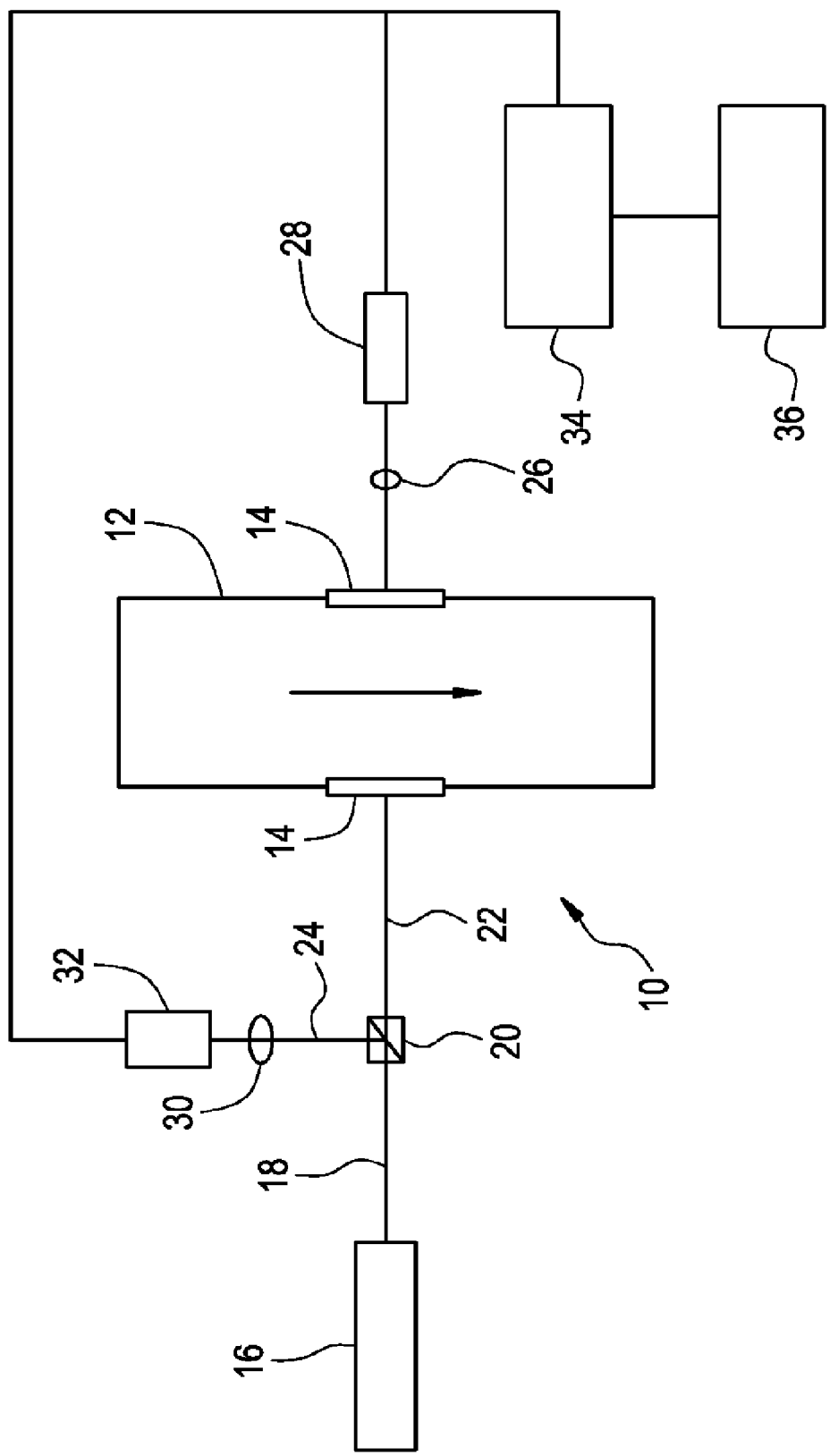
FIG. 1 is a schematic diagram of a system for measuring steam quality with a single narrow linewidth tunable diode laser in a accordance with an embodiment of this invention.

As summarized above, this invention encompasses methods and systems for measuring system quality. In particular, this invention encompasses a method for determining steam quality comprising passing one or more laser beams along a path through steam in a steam chamber. As explained above, steam typically includes a water vapor phase, which is gaseous water, and a liquid water phase, which is small droplets of water dispersed in the water vapor. The ratio of liquid water to water vapor in steam is a measure of steam quality.

As will be illustrated by the equations explained below, steam quality can be determined by direct measurements of laser radiation absorption by the water vapor phase and liquid water phase of steam. The water vapor and liquid water phase of steam have very different absorption properties. The water vapor absorption spectrum consists of narrow linewidth molecular roto-vibrational transitions, but liquid water has a much broader absorption spectrum. Thus, a sufficiently narrow linewidth excitation source excites a molecular transition in steam, but the absorption due to liquid water does affect the amplitude of the water vapor absorption peak. Instead, the absorption due to liquid water in the steam merely causes an offset in the baseline of the water vapor absorption peak. The amplitude of the peak and shift in baseline is used to determine absorption of laser beam radiation by water vapor and liquid water as will be explained in more detail as follows.

The molecular density in vapor (or liquid) phase is calculated using Beer-Lambert's relation given as:

$$\frac{I}{I_O} = \exp(-S_{\eta^*\eta'}(T)f(v, v_O, T, P)N_i L) \quad (1)$$

where, $I_O$ is the reference intensity, I is the transmitted intensity, $S_{\eta''\eta'}(T)$ is the line strength, $f(v, v_O, T, P)$ is the line shape function, $N_i$ is the molecular density and L is the path length of the beam. The line strength and the line shape functions of the laser radiation are dependent on the temperature and pressure, which is well documented in literature.

From equation 1, the molecular density can be written as:

$$N_i = \frac{\ln\left(\frac{I_O}{I}\right)}{S_{\eta^*\eta'}(T)\int_{v_1}^{v_2} f(v, v_O, T, P)L} \quad (2)$$

The above equation indicates that the molecular density is a function of reference and transmitted intensity. Using the above equation (2), the specific volume can be calculated as:

$$v = N_{av}/(N_i * MW_{H_2O}), \quad (3)$$

where $N_i = N_{WV} + N_{LW}$, $N_{WV}$ and $N_{LW}$ being the number of molecules of water vapor and liquid water respectively, they being calculated individually from Eq. 2, and $N_{av}$ is Avogadro's number.

For a two-phase liquid-vapor mixture, such as steam often is, the ratio of the mass of vapor present to the total mass of the mixture is its quality. Hence, steam quality is defined as $$X = \frac{m_{Vapor}}{m_{Liquid} + m_{Vapor}} \quad (4)$$

The value of quality ranges from zero to unity: at saturated liquid states, X=0, and at saturated vapor states, X=1.0. Although defined as a ratio, the quality is frequently given as a percentage.

The total volume of the mixture is the sum of the volumes of the liquid and vapor phases $$V = V_{Liquid} + V_{Vapor} \quad (5)$$

Dividing the above equation by the total mass of the mixture, m, an average specific volume for the mixture is obtained $$v = \frac{V}{m} = \frac{V_{Liquid}}{m} + \frac{V_{Vapor}}{m} \quad (6)$$

As the liquid phase is a saturated liquid and the vapor phase is a saturated vapor, therefore $$V_{Liquid} = m_{Liquid} v_L \text{ and } V_{Vapor} = m_{Vapor} v_V$$

Replacing the above relations in equation (6), we get $$v = \left(\frac{m_{Liquidd}}{m}\right)v_L + \left(\frac{m_{Vapor}}{m}\right)v_V \qquad (7)$$

Replacing the above equation with the definition of quality (X) as given in equation (4), we have $$v = v_L + X(v_V - v_L) \qquad (8)$$

Transforming the above equation, the quality is given as $$X = \frac{v - v_L}{v_V - v_L} \qquad (9)$$

Therefore, where steam exists as a two phase system at constant pressure, the steam quality value is given by equation (9).

Introducing the definition of specific volume using optical measurement from equation (3), we have steam quality defined as, $$X = \frac{\left[\frac{N_{av}}{(N_i * MW_{H_2O})}\right] - v_L}{v_V - v_L} \qquad (10)$$

From the above equation (10), it can be seen that the knowledge of specific volume of saturated liquid and specific volume of saturated vapor which is uniquely determined by the state conditions pressure (P) and temperature (T), and the average specific volume determined through the optical absorption technique gives the steam quality value for the two phase system.

Turning to FIG. 1, a single narrow linewidth laser steam quality measurement system 10 in accordance with an embodiment of this invention is illustrated. This steam quality measurement system 10 is operatively associated with a steam chamber 12 which can be a pipe or other steam conduit or housing that confines steam. This embodiment is particularly suitable for measuring steam quality of steam used in steam turbine generators. Thus, the steam chamber 12 can suitably be a steam chamber operatively associated with a steam turbine generator.

The steam chamber 12 includes a pair of glass windows 14 opposed to one another on opposite sides of steam chamber 12. In preferred embodiments, the windows 14 are of a type suitable for withstanding high temperatures and pressures experienced in a steam chamber. The windows 14 are positioned so that a laser beam can pass in a straight line from one window to the next and through the steam in between. Although not shown in FIG. 1, the steam quality measurement system 10 can further comprise a heater for heating the windows 14 sufficiently to reduce condensation of steam on the windows so that the condensation on the windows does not interfere with a laser beam passing through. Preferably, the windows 14 are heated to about 130° C. using heating tapes wound around flanges of the windows. Preferably, the windows 14 are made of quartz glass such as BK7 quartz glass having a thickness of about 6 mm.

The steam quality measurement system 10 further comprises a narrow linewidth laser 16 for directing a laser beam 18 through the glass windows 14 and the steam in the steam chamber 12. The laser 16 is suitable for frequency-scanning the laser beam 18 along a path through the steam in the steam chamber 12 to excite a molecular transition in the steam. The linewidth of the laser 16 corresponds to the frequency uncertainty of the laser. Desirably, the narrow linewidth laser 16 has a tuning range wavelength of 1366 nm to 1640 nm. In a preferred embodiment, the narrow linewidth laser 16 is a capable of frequency-scanning the laser beam 18 at a wavelength from 1383.8 nm to 1384.2 nm to excite the two molecular transitions in steam. Desirably, the narrow linewidth laser 16 is capable of emitting a laser beam having a linewidth of less than or equal to 0.0075 nm, more preferably less than or equal to 0.005 nm, and even more preferably less than or equal to 0.0001 nm. Tunable single mode diode lasers can go down to linewidths as low as 3.2 e-6 nm. Thus, the minimum linewidth of the narrow linewidth laser 16 is 3.2 e-6 nm. Desirably, the minimum linewidth of the narrow linewidth laser 16 is 0.0075 nm.

In a preferred embodiment, the narrow linewidth laser 16 is a narrow linewidth single mode tunable diode laser, and even more particularly is a New Focus 6300 series external cavity tunable diode laser with a wavelength range from 1366.68 to 1440.20 nm. The output power of such a laser varies from 9 mW at 1366.68 nm to 16 mW at 1440.2 nm. The laser has an rms linewidth of approximately 200 kHz and the output is a Gaussian TEM00 (transverse electromagnetic mode), meaning the laser radiates in a single transverse and longitudinal mode only. The laser is tunable, meaning that its frequency (wavelength) can be scanned continuously in the aforementioned wavelength range. The laser uses a Littman-type external cavity configuration for mode-hop free scanning over the entire wavelength range specified.

In a preferred embodiment, the laser 16 is coupled with optic fibers for beam transmission and conditioning to reduce laser beam misalignment and the use of free space laser beams.

A beam splitter 20 is positioned between the laser 16 and the windows 14 of the steam chamber 12 for splitting the laser beam 18 into a first part 22, which passes through the glass windows 14 and the steam in the steam chamber, and a second part 24 which passes through ambient air outside the steam chamber. The first part 22 of the laser beam 18 passes through a first spherical lens 26 after passing through the steam chamber 12 and then passes to a first photodetector 28 for measuring the transmitted intensity (I) of the first part 22 of the laser beam 18. The second part 24 of the laser beam 18 passes from the beam splitter 20 to a second spherical lens 30 and then to a second photodetector 32 for measuring the reference intensity ($I_o$) of the laser beam 18 in the ambient air outside of the steam chamber 12.

A digital oscilloscope 34 receives intensity data from the first and second photodetectors 28 and 32 and determines absorbance of laser radiation in the laser beam by the steam and by the ambient air to determine a reference absorption. A computer processor receives data from the digital oscilloscope 34 on absorption, determines a total number of water vapor molecules and liquid water molecules in the laser beam path, determines specific volumes of the water vapor phase and the liquid water phase in the steam, and calculates the steam quality based on the specific volumes. This is described in more detail below.

To measure the steam quality with the single laser steam quality measurement system 10, the narrow linewidth laser 16 emits the laser beam 18 and frequency-scans the laser beam at a wavelength from 1383.8 to 1384.2 nm to excite two molecular transitions in the water vapor phase of the steam. The beam splitter 20 splits the laser beam 18 into the first part 22, which passes through the windows 14 and the steam in the steam chamber 12 and through the first spherical lens 26 to the first photodetector 28. The first photodetector measures the transmitted intensity (I) of the first part 22 of the laser beam 18 over the scanned wavelengths and transmits the data to the digital oscilloscope 34. The measurement of the transmitted intensity of the laser beam 18 through the steam determines a peak absorption amplitude of the water vapor phase in the steam as the laser beam passes through the steam.

The second part 24 of the laser beam 18 passes from the beam splitter 20 through the second spherical lens 30 to the second photodetector 32 which measures the reference intensity ($I_o$) of the second part 24 of the laser beam as the laser beam passes through the ambient air. The digital oscilloscope 34 receives this reference intensity data from the second photodetector 32. The reference intensity from the second photodetector 32 determines a reference peak absorption amplitude which is used to normalize the peak absorption amplitude of the water vapor phase in the steam.

Furthermore, the intensity data from the first and second photodetectors 28 and 32 is used to determine a dc level of the peak absorption amplitude of the water vapor phase and the dc level of the reference peak absorption amplitude, respectively. The dc level of the peak absorption amplitude is then used to normalize the dc level of the peak absorption amplitude of the water vapor phase in the steam to thereby determine a shift in the dc level of the peak absorption amplitude of the water vapor phase from the dc level of the referenced peak absorption amplitude. A computer processor 36 then determines a total number of water molecules in the laser beam path through the steam based on the shift in the dc level of the peak absorption amplitude of the water vapor phase using Beer Lambert's law. The computer processor 36 then determines specific volumes of the water vapor phase and the liquid water phase in the steam using the total numbers of water vapor and liquid water molecules and then calculates the quality of the steam based on the specific volumes of the water vapor phase and the liquid water phase in the steam.

Figure 2:
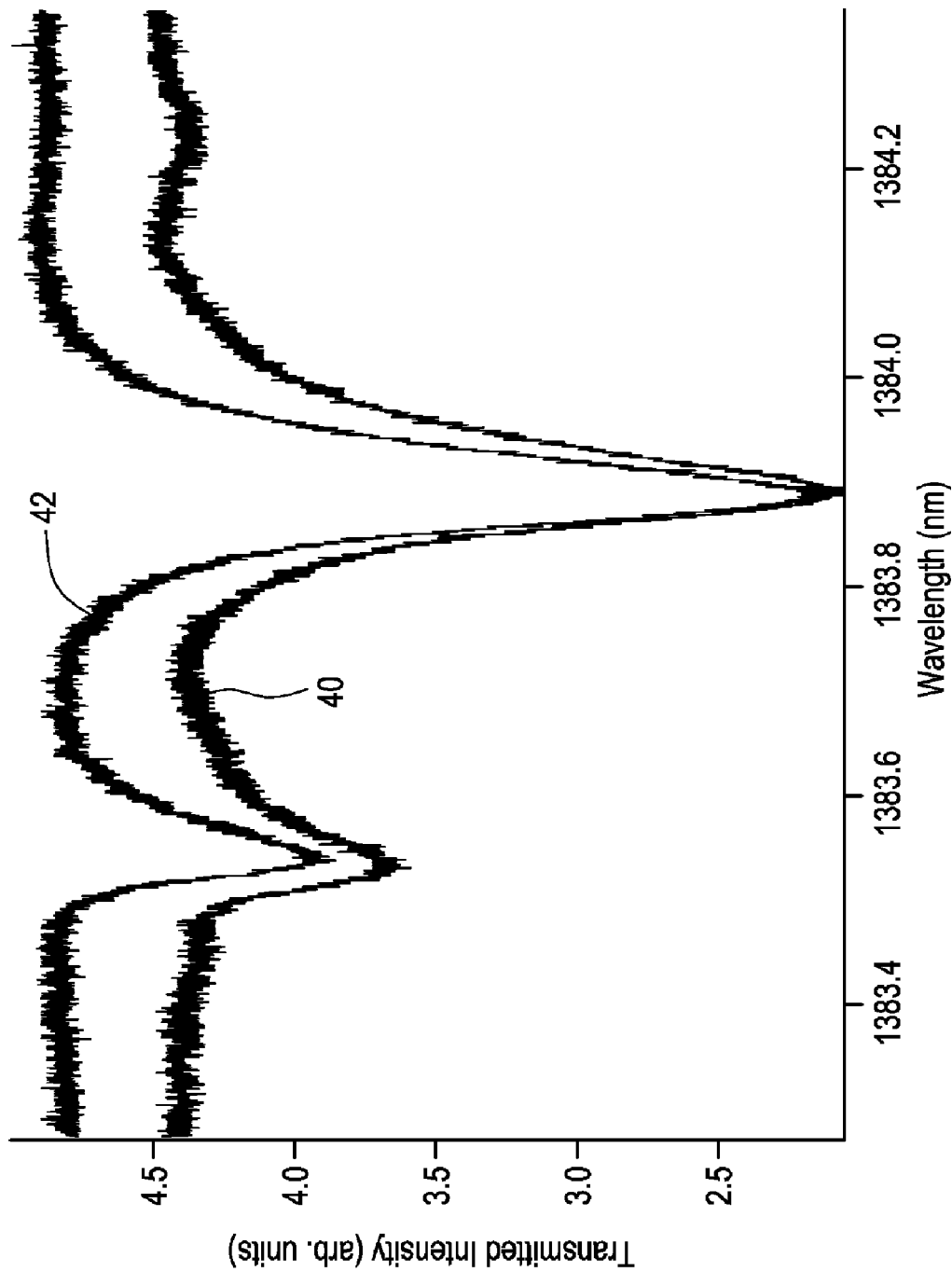
FIG. 2 is a graph of the transmitted intensity of a narrow linewidth laser beam versus wavelength of the laser beam through steam and ambient air.

FIG. 2 illustrates graphically the transmitted intensity of a laser beam passing through steam versus wavelength of the laser beam radiation. The plot 40 of transmitted intensity of a laser beam through steam is shown along with a plot 42 of transmitted intensity of a laser beam through ambient air. The plot 42 of transmitted intensity of a laser beam through ambient air serves as a reference plot. As can be seen from FIG. 2, the plot 40 of the transmitted intensity of the laser beam through steam is shifted from the plot 42 of the transmitted intensity of the laser beam through water vapor in the ambient air.

The single laser steam quality measurement system 10 provides for real-time measurement of steam quality using optics and can measure steam quality at any flow rates and is non-invasive. This embodiment is also reasonably economical and easy to implement.

Figure 3:
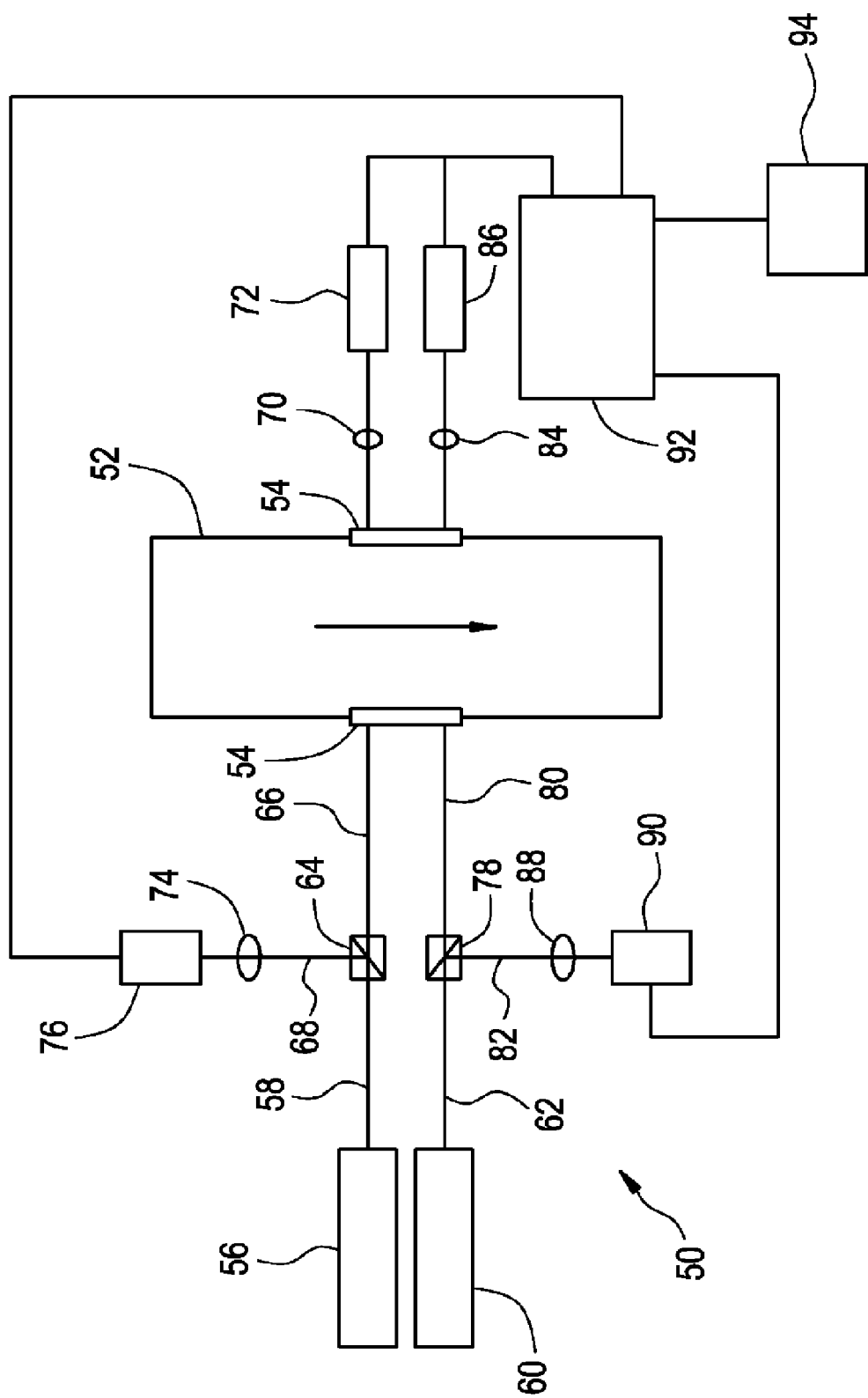
FIG. 3 is a schematic diagram of a steam quality measurement system using multiple broadband lasers in accordance with another embodiment of this invention.

Turning to FIG. 3, a multiple laser steam quality measurement system 50 is illustrated. This measurement system 50 is optically associated with a steam chamber 52 which is a pipe or other conduit or housing that confines steam and may advantageously be part of a steam turbine generator. The steam chamber 52 comprises a pair of glass windows 54 mounted opposite one another for clear transmission of a laser through the windows and the steam in between. The type of glass for the windows and the use of a heater (not shown) are the same as described for the single laser system 10 described hereinabove.

The multiple laser steam quality measurement system 50 further comprises a first broadband laser 56 for emitting a first laser beam 58 at a first wavelength along a path through the windows 54 and the steam in the steam chamber. The wavelength of the first laser beam 58 should be such that the water vapor phase in the steam absorbs radiation in the first laser beam at a high level and the liquid water phase in the steam absorbs radiation in the first laser beam at a level substantially lower than the high level of absorption by the water vapor phase. In a particular embodiment, the wavelength to the first laser beam ranges from 900 nm to 980 nm, and in a more particular embodiment is at a wavelength 945 nm.

The multiple laser steam quality measurement system 50 also comprises a second broadband laser 60 for emitting a second laser beam 62 at a second wavelength along a path through the windows 54 and the steam in the steam chamber 52. The wavelength of the second laser beam 62 is different from the wavelength of the first laser beam 58 and is such that the liquid water phase in the steam absorbs radiation in the second laser beam at a high level and the water vapor phase absorbs radiation in the second laser beam at a level substantially lower than the high level of absorption by the liquid water phase in the steam. In particular embodiments of the invention, the wavelength of the second laser beam ranges from 1300 nm to 2000 nm, and in a particular embodiment has a wavelength of 1560 nm. The linewidth of the first laser beam 58 is desirably less than or equal to 5 nm and the linewidth of the second laser beam is desirably less than or equal to 15 nm. More preferably, the linewidth of the first laser beam 58 is less than or equal to 1 nm and the linewidth of the second laser beam 62 is less than or equal to 3 nm. Even more preferably, the linewidth of the first laser beam 58 is less than or equal to 0.1 nm and the linewidth of the second laser beam 68 is less than or equal to 0.5 nm. Broadband lasers typically have a minimum linewidth of about 0.2 nm, thus the minimum linewidth of the first and second laser beams is about 0.2 nm.

In a preferred embodiment, the first and second broadband lasers 56 and 60 are coupled with optic fibers for beam transmission and conditioning to reduce laser beam misalignment and the use of free space laser beams.

The first laser beam 58 passes from the first broadband laser 56 through a first beam splitter 64 which splits the laser beam into a first part 66 and a second part 68. The first part 66 of the first laser beam 58 passes from the first beam splitter 64 through the glass windows 64 and the steam in the steam chamber 52 and thereafter through a first spherical lens 70 to a first photodetector 72. The first photodetector 72 measures the transmitted intensity (I) of the first part 66 of the first laser beam 58.

The second part 68 of the first laser beam 58 passes from the first splitter 64 through a second spherical lens 74 to a second photodetector 76. The second photodetector 76 measures the reference transmitted intensity ($I_o$) of the second part 68 of the first laser beam 58 as it passes through water vapor in the ambient air.

The second laser beam 62 passes from the second broadband laser 60 through a second beam splitter 78 which splits the second laser beam into a first part 80 and a second part 82. The first part 80 of the second laser beam 62 passes from the second splitter 78 through the glass windows 54 and the steam in the steam chamber 52 and thereafter through a third spherical lens 84 to a third photodetector 86. The third photodetector 86 measures the transmitted intensity of the first part 80 of the second laser beam 62. The second part 82 of the second laser beam 62 passes from the second beam splitter 78 through a fourth spherical lens 88 to a fourth photodetector 90. The fourth photodetector 90 measures the transmitted intensity of the second part 82 of the second laser beam 62 after the second part of the second laser beam passes through water vapor in the ambient air.

A digital oscilloscope 92 receives data from the first photodetector 72, the second photodetector 76, the third photodetector 86, and the fourth photodetector 90. The digital oscilloscope 92 determines the absorbance of radiation from the first and second laser beams 58 and 68 through the steam and through the ambient air. A computer processor 94 normalizes the transmitted powers of the first and second laser beams 58 and 62 through the steam based on the transmitted powers of the first and second laser beams through the ambient air, determines the total number of water vapor and liquid water molecules based on such normalized transmitted powers, determines specific volumes of the water vapor phase and the liquid water phase in the steam and calculates the quality of the steam based on such specific volumes. This is explained in more detail below.

To measure the steam quality using the multiple laser steam quality measurement system 50, the first and second laser beams 58 and 62 are emitted from the first and second broadband lasers 56 and 60 at wavelengths of 945 nm and 1560 nm, respectively. Desirably, the first broadband laser 56 has a linewidth of 2 nm and a power of about 20 mW and the second broadband laser 60 has a linewidth of 10 nm and a power of about 20 mW. The first laser beam 58 passes from the first broadband laser 56 through the first beam splitter 64. The first part 66 of the first laser beam 58 passes from the first beam splitter 64 through the glass windows 54 and the steam in the steam chamber 52 and thereafter through the first spherical lens 70 to the first photodetector 72. The first photodetector 72 measures the transmitted intensity (I) or power of the first part 66 of the first laser beam 62 and transmits that data to the digital oscilloscope 92 which measures the absorbance of radiation in the first part 66 of the first laser beam 58 through the water vapor phase in the steam. Because of the wavelength of the first laser beam 58, the absorbance of the radiation is primarily by the water vapor phase in the steam.

The second part 68 of the first laser beam 58 passes from the first beam splitter 64 through the second spherical lens 74 to a second photodetector 76. The second part 68 of the first laser beam 58 passes through the ambient air outside the steam chamber 52 and the second photodetector 76 measures the transmitted intensity of the second part 68 of the first laser beam 58. These data are transmitted to the oscilloscope 92 which determines the absorbance of radiation in the second part 68 of the first laser beam 58 by water vapor in the ambient air. The absorbance of water vapor in the ambient serves as a reference for the absorbance of water vapor in the steam measured by the first photodetector 72 and is used to normalize the transmitted intensity or power of the first part 66 of the first laser beam 58 through the steam in the steam chamber 52.

The second laser beam 62 is emitted from the second broadband laser 60 at a wavelength of 1 560 nm and passes through the second beam splitter 78. The second beam splitter 78 splits the second laser beam 62 into a first part 80 and a second part 82. The first part 80 of the second laser beam 62 passes from the second splitter 78 through the glass windows 58 and the steam in the steam chamber 52 and thereafter a third spherical lens 84 to a third photodetector 86. The third photodetector 96 measures the transmitted intensity or power of the first part 80 of the second laser beam 62. These data are transmitted to the digital oscilloscope 92 which determines the absorbance of radiation in the first part 80 of the second laser beam 62 by the liquid water phase of the steam in the steam chamber 52. Because of the wavelength of the second laser beam 62, this absorbance is primarily of the liquid water phase in the steam.

The second part 82 of the second laser beam 62 passes from the second beam splitter 78 through the fourth spherical lens 88 to a fourth photodetector 90 which measures the transmitted intensity or power of the second part 82 of the second laser beam 62 through water vapor in the ambient air outside of the steam chamber 52. These data are transmitted to the digital oscilloscope 92 which determines the absorbance of the second part 82 of the second laser beam 62 by water vapor in the ambient air. This absorbance serves as a reference absorbance for the absorbance of the liquid water phase in the steam. This reference absorbance is used to normalize the transmitted intensity or power of the first power 80 of the laser beam 62 through the steam.

Using Beer Lambert's law, the computer processor 94 determines a total number of water vapor molecules in the path of the first laser beam 58 based on the normalized transmitted intensity of the first laser beam through the steam and determines a total number of liquid water molecules in the path of the second laser beam 62 based on the normalized transmitted intensity of the second beam through the steam, determines specific volumes of the water vapor phase and the liquid vapor phase in the steam using the total numbers of water vapor and liquid water molecules, and calculates the quality of the steam based on the specific volumes of water vapor phase and liquid water phase in the steam.

As with the previous embodiment, the multiple laser steam quality measurement system 50 provides for real-time measurement of steam quality using optical techniques, can measure steam quality at any flow rate, is non-invasive, and is relatively economical.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

What is claimed is:

1. Method for determining steam quality comprising the steps of:

passing a first laser beam at a first wavelength emitted from a first broadband laser along a path through steam in a steam chamber, the steam having a water vapor phase and a liquid water phase, the first wavelength such that the water vapor phase absorbs radiation in the first laser beam at a high level and the liquid water phase absorbs radiation in the first laser beam at a level substantially lower than the high level of absorption by the water vapor phase;

passing a second laser beam at a second wavelength emitted from a second broadband laser along a path through the steam in the steam chamber, the second wavelength different from the first wavelength and such that the liquid water phase absorbs radiation in the second laser beam at a high level and the water vapor phase absorbs radiation in the second laser beam at a level substantially lower than the high level of absorption by the liquid water phase;
measuring the transmitted intensity of the first laser beam through the steam;
measuring the transmitted intensity of the second laser beam through the steam;
normalizing the transmitted intensities of the first and second laser beams through the steam;
using Beer Lambert's law, determining a total number of water vapor molecules in the path of the first laser beam based on the normalized transmitted intensity of the first laser beam through the steam;
using Beer Lambert's law, determining a total number of liquid water molecules in the path of the second laser beam based on the normalized transmitted intensity of the second laser beam through the steam;
determining specific volumes of the water vapor phase and the liquid water phase in the steam using the total numbers of water vapor and liquid water molecules; and
calculating quality of the steam based on the specific volumes of water vapor phase and liquid water phase in the steam.

2. Method as in claim 1 wherein the first laser beam has a wavelength from 900 nm to 980 nm and the second laser beam has a wavelength from 1300 nm to 2000 nm.

3. Method as in claim 1 wherein the first laser beam has a wavelength of 945 nm and the second laser beam has a wavelength of 1560 nm.

4. Method as in claim 1 wherein:
the step of passing the first laser beam through the steam comprises splitting the first laser beam into a first part which passes through the steam and a second part which is diverted along a path through ambient air outside of the chamber;
the step of passing the second laser beam through the steam comprises splitting the second laser beam into a first part which passes through the steam and a second part which is diverted along a path through ambient air outside of the chamber;
the method further comprises the step of measuring the transmitted intensity of the second part of the first laser beam through the ambient air;
the method further comprises the step of measuring the transmitted intensity of the second part of the second laser beam through the ambient air;
the step of normalizing the transmitted intensities of the first and second laser beams through the steam comprises normalizing the transmitted intensities of the first and second laser beams through the steam with respect to the measured transmitted intensity of the second part of the first laser beam through the ambient air and the measured transmitted intensity of the second part of the second laser beam through the ambient air, respectively.

5. Method as in claim 1 wherein the first laser beam has a linewidth of less than or equal to 5 nm and the second laser beam has a linewidth of less than or equal to 15 nm.

6. Method as in claim 1 wherein the first laser beam has a linewidth of less than or equal to 1 um and the second laser beam has a linewidth of less than or equal to 3 nm.

7. Method as in claim 1 wherein the first laser beam has a linewidth of less than or equal to 0.1 nm and the second laser beam has a linewidth of less than or equal to 0.5 nm.

8. Method as in claim 1 wherein the chamber comprises glass windows for transmission of the laser beam through the steam and the method further comprises heating the glass windows to reduce steam condensation on the windows.

9. Method as in claim 8 wherein the glass windows are high-transmission quartz glass windows.

10. Method as in claim 1 wherein the chamber is part of a steam turbine system.

11. Method as in claim 1 wherein the first and second broadband lasers are coupled with optic fibers for laser beam transmission and conditioning.

12. System for determining steam quality comprising:
a chamber for containing steam, the steam having a water vapor phase and a liquid water phase;
a first broadband laser operatively associated with the chamber for passing a first laser beam at a first wavelength along a path through steam in the steam chamber, the first wavelength such that the water vapor phase absorbs radiation in the first laser beam at a high level and the liquid water phase absorbs radiation in the first laser beam at a level substantially lower than the high level of absorption by the water vapor phase;
a second broadband laser operatively associated with the chamber for passing a second laser beam at a second wavelength along a path through steam in the steam chamber, the second wavelength different from the first wavelength and such that the liquid water phase absorbs radiation in the second laser beam at a high level and the water vapor phase absorbs radiation in the second laser beam at a level substantially lower than the high level of absorption by the liquid water phase;
a first photodetector for measuring the transmitted intensity of the first laser beam through the steam;
a second photodetector for measuring the transmitted intensity of the second laser beam through the steam; and
a computer processor for:
normalizing the transmitted intensities of the first and second laser beams through the steam;
using Beer Lambert's law, determining a total number of water vapor molecules in the path of the first laser beam based on the normalized transmitted intensity of the first laser beam through the steam;
using Beer Lambert's law, determining a total number of liquid water molecules in the path of the second laser beam based on the normalized transmitted intensity of the second laser beam through the steam;
determining specific volumes of water vapor phase and liquid water phase in the steam using the total numbers of water vapor and liquid water molecules; and
calculating quality of the steam based on the specific volumes of water vapor phase and liquid water phase in the steam.

13. System as in claim 12 wherein the first laser is capable of emitting a laser beam having a wavelength from 900 nm to 980 nm and the second laser is capable of emitting a laser beam having a wavelength from 1300 nm to 2000 nm.

14. System as in claim 12 wherein the first laser is capable of emitting a laser beam having a wavelength of 945 nm and the second laser is capable of emitting a laser beam having a wavelength of 1560 nm.

15. System as in claim 12 further comprising:
a first laser beam splitter for splitting the first laser beam into a first part which passes through the steam and a second part which is diverted along a path through ambient air outside of the chamber;
a second laser beam splitter for splitting the second laser beam into a first part which passes through the steam and a second part which is diverted along a path through ambient air outside of the chamber;

a third photodetector for measuring the transmitted intensity of the second part of the first laser beam through the ambient air; and a fourth photodetector for measuring the transmitted intensity of the second part of the second laser beam through the ambient air.

16. System as in claim 15 further comprising a computer processor for:

normalizing the transmitted intensities of the first and second laser beams through the steam with respect to the measured transmitted intensity of the second part of the first laser beam through the ambient air and the measured transmitted intensity of the second part of the second laser beam through the ambient air, respectively;

using Beer Lambert's law, determining a total number of water vapor molecules in the path of the first laser beam based on the normalized transmitted intensity of the first laser beam through the steam;

using Beer Lambert's law, determining a total number of liquid water molecules in the path of the second laser beam using Beer Lambert's law based on the normalized transmitted intensity of the second laser beam through the steam;

determining specific volumes of water vapor phase and liquid water phase in the steam using the total numbers of water vapor and liquid water molecules; and calculating quality of the steam based on the specific volumes of water vapor phase and liquid water phase in the steam.

17. System as in claim 15 further comprising an oscilloscope for determining peak absorption amplitude of the water vapor phase as the first part of the first laser beam passes through the steam, peak absorption amplitude of the liquid water phase as the first part of the second laser beam passes through the steam, peak absorption amplitude of water vapor in the ambient air as second part of the first laser beam passes through the ambient air to determine a reference peak absorption amplitude for water vapor, and peak absorption amplitude of liquid water in the ambient air as second part of the second laser beam passes through the ambient air to determine a reference peak absorption amplitude for liquid water.

18. System as in claim 12 wherein the first broadband laser is capable of emitting the first laser beam with a linewidth of less than or equal to 5 nm and the second broadband laser is capable of emitting the second laser beam with a linewidth of less than or equal to 15 nm.

19. System as in claim 12 wherein the first broadband laser is capable of emitting the first laser beam with a linewidth of less than or equal to 1 nm and the second broadband laser is capable of emitting the second laser beam with a linewidth of less than or equal to 3 nm.

20. System as in claim 12 wherein the first broadband laser is capable of emitting the first laser beam with a linewidth of less than or equal to 0.1 nm and the second broadband laser is capable of emitting the second laser beam with a linewidth of less than or equal to 0.5 nm.

21. System as in claim 12 wherein the chamber comprises glass windows for transmission of the laser beam through the steam and the system further comprises a heater for heating the glass windows to reduce steam condensation on the windows.

22. System as in claim 21 wherein the glass windows are high-transmission quartz glass windows.

23. System as in claim 12 wherein the first and second broadband lasers are coupled with optic fibers for laser beam transmission and conditioning.

24. A steam turbine comprising a system for measuring steam quality as in claim 12.

* * * * *